United States Patent [19]

Veber et al.

[11] 4,191,754
[45] Mar. 4, 1980

[54] BICYCLIC SOMATOSTATIN ANALOGS

[75] Inventors: Daniel F. Veber, Ambler; Ruth F. Nutt, Green Lane, both of Pa.

[73] Assignee: Merck & Co., Inc., Rahway, N.J.

[21] Appl. No.: 16,218

[22] Filed: Feb. 28, 1979

[51] Int. Cl.² .................. A61K 37/100; C07C 103/52
[52] U.S. Cl. ............................ 424/177; 260/112.5 S;
[58] Field of Search ................. 260/112.5 S, 112.5 R; 424/177

[56] References Cited

U.S. PATENT DOCUMENTS

| 4,010,260 | 3/1977 | Immer et al. | 260/112.5 S |
|---|---|---|---|
| 4,115,554 | 9/1978 | Ueber | 260/112.5 R |
| 4,139,526 | 2/1979 | Ueber | 260/112.5 R |
| 4,140,767 | 2/1979 | Ueber | 260/112.5 S |

Primary Examiner—Delbert R. Phillips
Assistant Examiner—Blondel Hazel
Attorney, Agent, or Firm—David L. Rose; Harry E. Westlake, Jr.

[57] ABSTRACT

Bicyclic somatostatin analogs and pharmaceutically acceptable non-toxic acid addition salts thereof are prepared by a combination of the solid phase method and the solution method. These analogs have the property of inhibiting the release of insulin, glucagon and growth hormone in humans and animals. The compounds are particularly useful in the treatment of diabetes. Due to the bicyclic structure, these analogs are resistant to enzymatic metabolism and have a longer duration of activity.

10 Claims, No Drawings

BICYCLIC SOMATOSTATIN ANALOGS

BACKGROUND OF THE INVENTION

Somatostatin is a tetradecapeptide having the structure:

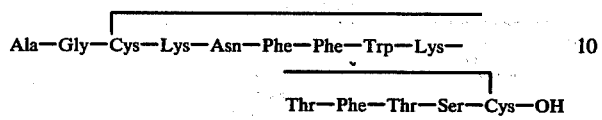

and has the properties of inhibiting the release of growth hormone, inhibiting the release of insulin and glucagon and reducing gastric secretion. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself.

The present invention provides bicyclic somatostatin analogs having higher biological activities and a longer duration of action than somatostatin and a novel method for preparing said analogs.

SUMMARY OF THE INVENTION

This invention is concerned with novel bicyclic somatostatin analogs having a more potent biological activity and a longer duration of action than naturally occurring somatostatin having the structural formula:

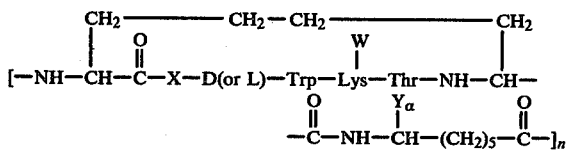

wherein
- n is 1 or 2;
- X is Phe or Tyr;
- Y is H or COOH; and
- when Y is COOH, the carbon atom designated α in aminosuberyl is D- or L-;
- W on the ε-amino group of lysine is independently selected from H or INOC and pharmaceutically acceptable non-toxic acid addition salts thereof.

Included in the present invention are novel compounds having the structure:

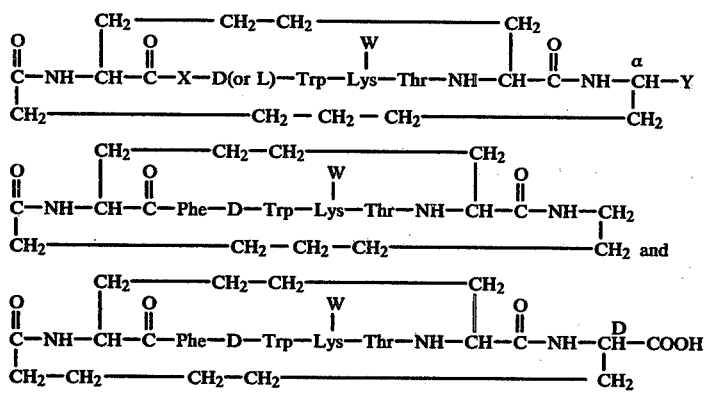

wherein
W, X, Y and α are as defined above.

Also included in the present invention are the novel compounds having the structure:

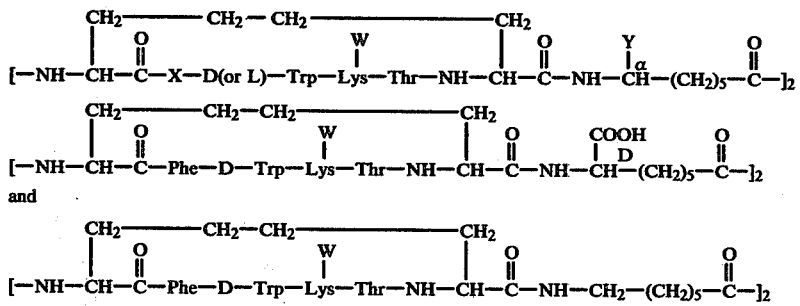

wherein
W, X, Y and α are as defined above.

The preferred bicyclic somatostatin analogs of the present invention are illustrated by the following structural formula:

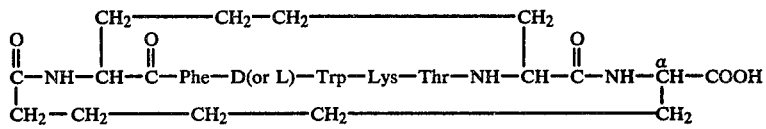

wherein the carbon designated α in aminosuberyl is D- or L- and pharmaceutically acceptable non-toxic acid addition salts thereof.

Still further preferred bicyclic somatostatin analogs are those having the structural formula:

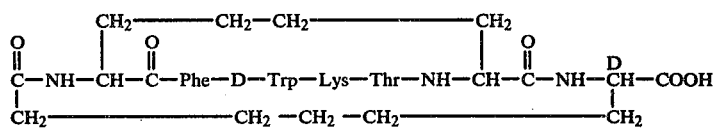

wherein D refers to the D-isomer.

Included in the present invention are the novel straight chain and mono-cyclic intermediates having the structural formula:

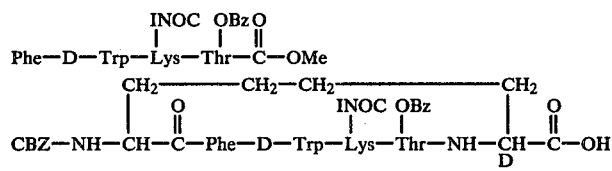

Included in the present invention is a novel electrolytic oxidative process for the preparation of

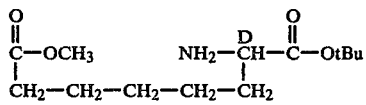

Illustrative of acid addition salts are hydrochloride, hydrobromide, sulfate, phosphate, maleate, acetate, citrate, benzoate, succinate, malate, ascorbate and the like. The acid addition salts can be conveniently prepared by dissolving the above novel compounds in water, adding two equivalents of appropriate acid and lyophilizing.

The bicyclic somatostatin analogs of the present invention differ from somatostatin by virtue of the fact that they lack an N-terminal amino group thus eliminating the group involved in enzymic cleavage of the molecule by aminopeptidases. Further stability is provided by the bicyclic rings themselves; the presence of these rings increases the rigidity of the molecule and reduces its susceptibility to enzymatic metabolism. The absence of a disulfide bridge also retards metabolism. Therefore, the analogs of the present invention are more resistant to cleavage in vivo than somatostatin and thus have a prolonged duration of action.

The abbreviated designations, which are used herein for the amino acid components, certain preferred protecting groups, reagents and solvents employed in the process of this invention are as follows:

TABLE I

| Abbreviated Designation | Amino acid |
|---|---|

TABLE I-continued

| Abbreviated Designation | |
|---|---|
| Lys | L-lysine |
| Phe | L-phenylalanine |
| Trp | L-tryptophan |
| D-Trp | D-tryptophan |
| Thr | L-threonine |
| Tyr | L-tyrosine |
| Asu | D- or L-α-aminosuberic acid |
| Dsu | diaminosuberic acid |
| | Protecting Groups |
| INOC | isonicotinyloxycarbonyl |
| BOC | tert-butyloxycarbonyl |
| OMe | methyl ester |
| tBu | tert-butyl |
| CBZ | benzyloxycarbonyl |
| Bzl | benzyl |
| | Condensing Agents |
| DCCI | dicylcohexylcarbodiimide |
| | Reagents |
| DPPA | diphenylphosphoryl azide |
| TFA | trifluoroacetic acid |
| TEA | triethylamine |
| DIPEA | diisopropylethylamine |
| MgSO$_4$ | magnesium sulfate |
| HBT·H$_2$O | 1-hydroxybenzotriazole monohydrate |
| NH$_2$NH$_2$ | hydrazine, 95% |
| | Solvents |
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |
| CH$_2$Cl$_2$ | methylene chloride |
| EtOAc | ethylacetate |
| CMA | chloroform-methanol-concentrated ammonium hydroxide |
| CHCl$_3$ | chloroform |
| i-PrOH | isopropanol |

EXAMPLE 1

Preparation of BOC-Phe-D-Trp-(INOC)Lys-(O-Bzl)Thr-OMe

Chloromethyl resin (2% cross-linked Merrifield resin), 80 g (0.211 moles), having 2.64 meq. chlorine/g, and 65.4 g (0.211 moles) of BOC-(O-Bzl)Thr were added to 600 ml of peroxide-free tetrahydrofuran. The mixture was stirred in an oil bath at 80° C. bath temperature for 1 hour. Triethylamine, 27.7 ml, was added and the reaction mixture stirred at 80° C. bath temperature for 70 hours, cooled to 25° C. and filtered and washed with:

3×300 ml of tetrahydrofuran
4×500 ml of ethanol
1×500 ml of acetic acid
3×500 ml of water
3×500 ml of methanol
3×500 ml of chloroform The BOC-(O-Bzl)Thr-O-CH$_2$-$\phi$-resin was dried in vacuo at 40° C. for 16 hours, giving 115.9 g of BOC-(O-Bzl)-Thr-O-CH$_2$-$\phi$-resin containing 0.795 mmole of Thr/g of resin.

BOC-(O-Bzl)Thr-O-CH$_2$-$\phi$-resin (5.03 g, 4.0 mmole) was carried through the procedure in Tables III and IV using 2 deblockings (2 minutes and 25 minutes) with 25% TFA in methylene chloride in the presence of 1% ethanedithiol and 2.5 equivalents of BOC-amino acid in the required sequence until the desired blocked tetrapeptide-O-CH$_2$-$\phi$-resin was obtained.

DCCI was used as the sole coupling agent in every step except the recoupling step in which case the coupling was carried out with DCCI in the presence of 1-hydroxybenzotriazole monohydrate (HBT.H$_2$O).

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr was blocked with Bzl; and the ε-amino group of Lys with INOC.

|  | Found μm/mg of peptide resin |
|---|---|
| Lys | 0.548 |
| Thr | 0.430 (uncorr.) |
| Phe | 0.549 |

BOC-Phe-D-Trp-(INOC)Lys-(O-Bzl)Thr-O-CH$_2$-$\phi$-resin, 8.9 g, in 350 ml methanol was treated with 29 ml triethylamine for 92 hours at room temperature with magnetic stirring. Filtration and evaporation of the solvent yielded 5.2 g of crude product which was purified on a 600 g silica gel column by elution with 5% isopropanol in chloroform. Two liters of solvent were collected before starting the collection of 70 ml fractions. The product was eluted in fractions 137 to 270. These fractions were combined and evaporated to give 3.0 g of product.

A 20 hour acid hydrolysate gave the following amino acid analysis:

|  | Found μm/mg | Normalized to the Average |
|---|---|---|
| Lys | 0.961 | 0.97 |
| NH$_3$ | 0.09 | 0.09 |
| Thr | 1.03 | 1.03 |
| Phe | 0.940 | 0.95 |
| Trp | 1.05 | 1.05 |

R$_f$ 0.6 in 90:10:0.5 (CHCl$_3$: isopropanol: water).

EXAMPLE 2

Preparation of
Phe-D-Trp-(INOC)Lys-(O-Bzl)Thr-OMe.2HCl

Three g of BOC-Phe-D-Trp-(INOC)Lys-(O-Bzl)Thr-OMe, prepared by the process of Example 1, in 75 ml of ethyl acetate were treated at −30° C. with a

TABLE III

| Solvent or reagent (number of treatments or washes) | CHCl$_3$ (2) | 25% TFA in CH$_2$Cl$_2$ + 1% ethanedithiol (2) * | CHCl$_3$ (3) | NEt$_3$-CH$_2$Cl$_2$ (1:9) (2) | CHCl$_3$ (3) CH$_2$Cl$_2$ (3) | BOC AA in CH$_2$Cl$_2$ DMF or a mixture of both | 0.5M DCCI in CH$_2$Cl$_2$ | DMF (1) MeOH (1) DMF (1) MeOH (1) CHCl$_3$ (2) |
|---|---|---|---|---|---|---|---|---|
| Volume in ml. | 60 | 60 | 60 | 60 | 60 | 45 | 20 | 60 |
| Time in min. | 5 | 2 and 25 | 2 | 5 and 5 | 2 | 5 coupling 30 | 5 | 2 |

*1% ethanedithiol was not used until the deblocking of BOC-D-Trp-(INOC)Lys-(O-Bzl)Thr-O-CH$_2$-$\phi$-resin.

TABLE IV

| Protected Amino Acid |  | Solvent ml |
|---|---|---|
| BOC-(INOC)Lys recouple* | (3.81 g) | DMF, 22 ml CH$_2$Cl$_2$, 23 ml |
| BOC-D-Trp recouple* | (3.04 g) | CH$_2$Cl$_2$, 35 ml DMF, 10 ml |
| BOC-Phe recouple* | (2.65 g) | CH$_2$Cl$_2$, 45 ml |

*For each recoupling 20 mm of HBT . H$_2$O was added, using 45 ml DMF as solvent.

After the procedures of Tables III and IV were completed, the blocked tetrapeptide-O-CH$_2$-$\phi$-resin was dried overnight in vacuo and weighed 9.07 g.

A 4 hour 6 N HCl/propionic acid hydrolysis at 130° C. gave the following amino acid analysis:

stream of anhydrous HCl for 5 minutes and a stream of nitrogen for 5 minutes. The product was precipitated by the addition of 50 ml of ether and 100 ml petroleum ether. The solid was collected by filtration and dried in vacuo to give 2.77 g of product which was used without purification in the next step.

EXAMPLE 3

Preparation of
N$_\alpha$-CBZ-N$_{\alpha'}$-BOC-$\alpha'$-t-butylester-$\alpha$-diaminosuberyl-Phe-D-Trp-(INOC)Lys-(O-Bzl)-Thr-OMe To 2.9 g (3.14 mmole) of Phe-D-Trp-(INOC)-Lys-(O-Bzl)Thr-OMe.2HCl, prepared by the process of Example 2 and 1.0 g of HBT.H$_2$O in 40 ml of CH$_2$Cl$_2$ was added 0.9 ml of TEA and a solution of 1.55 g of N$_\alpha$-CBZ-N$_{\alpha'}$-BOC-$\alpha'$-t-butyldiaminosuberate (prepared as in Example 20, U.S. Ser. No. 695,348, filed June 14, 1976) in 20 ml of CH$_2$Cl$_2$ and treated with 700 mg of DCCI for 2 hours at room temperature. During this time a total of 0.67 ml of TEA was added to keep the pH at 5.5. The suspension was filtered and the filtrate was extracted with water (3×75 ml). The CH$_2$Cl$_2$ layer was dried over anhydrous MgSO$_4$, filtered and the solvent evaporated to give 4.8 g of crude product.

The crude product was dissolved in a minimum amount of 95:5:0.2 (chloroform; isopropanol; water) and applied on a 500 g silica gel column packed in the same solvent. The product was eluted with the same solvent, collecting 70 ml cuts. Fractions 21 to 36 were combined to give 3.51 g of product.

A 20 hour acid hydrolysate gave the following amino acid analysis.

|  | Found μm/mg | Normalized to the Average |
|---|---|---|
| Lys | 0.723 | 1.00 |
| NH$_3$ | 0.140 | 0.19 |
| Thr | 0.724 | 1.01 |
| Phe | 0.708 | 0.98 |
| Trp | 0.476 | 0.66 |
| Dsu | 0.727 | 1.01 |

R$_f$ 0.25 in 95:5:0.2 (CHCl$_3$: isopropanol: water).

EXAMPLE 4

Preparation of
N$_\alpha$-CBZ-α-diaminosuberyl-Phe-D-Trp-(INOC)Lys-(O-Bzl)Thr-OMe A solution of 3.4 g of N$_\alpha$-CBZ-N$_{\alpha'}$-BOC-α'-t-butylester-α-diaminosuberyl-Phe-D-Trp-(INOC)-Lys-(O-Bzl)Thr-OMe in 87 ml of EtOAc and 0.87 ml of ethanedithiol was cooled to −30° C. and treated with a vigorous stream of anhydrous HCl for 35 minutes and a stream of N$_2$ for 8 minutes. The product was precipitated by the addition of excess ether and petroleum ether. The solid was collected by filtration and dried in vacuo to give 2.88 g of crude product.

R$_f$ 0.6, 70:30:3, (CMW)

EXAMPLE 5

Preparation of
N$_\alpha$-CBZ-α-diaminosuberyl-Phe-D-Trp-(INOC)Lys-(O-Bzl)Thr-NH-NH$_2$ 2.87 g of N$_\alpha$-CBZ-α-diaminosuberyl-Phe-D-Trp-(INOC)Lys-(O-Bzl)Thr-OMe prepared by the process of Example 4, was treated with 75 ml of a solution of DMF:NH$_2$NH$_2$ (2:1) at room temperature for 1 hour. The solution was evaporated to a small volume, the DMF was evaporated twice and the residue was triturated with 300 ml of EtOAc. The solid was filtered, washed with ether (3×100 ml) and dried overnight. The crude product was washed with water, until filtrates were negative to Tollen's test and the solid was dried in vacuo to give 2.56 g of the hydrazide.

R$_f$ 0.5, 70:30:3 (CMW)

EXAMPLE 6

Preparation of

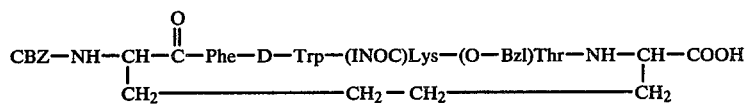

A solution of 2.43 g of N$_\alpha$-CBZ-α-diaminosuberyl-Phe-Trp-(INOC)Lys-(O-Bzl)Thr-NH-NH$_2$, prepared by the process of Example 5, in 50 ml DMF was cooled to −25° C., acidified with 1.54 ml of 5.5 M HCl in THF and treated with 0.378 ml of isoamyl nitrite for 1 hour. The azide solution was added to 2.4 liters of degassed DMF previously cooled to −40° C. and neutralized with 3.45 ml of DIPEA to a pH of 7.0 to 7.2. The reaction was kept at −20° C. for 24 hours and at +5° C. for 72 hours, during which period an additional 0.4 ml of DIPEA was added. The reaction was evaporated to a small volume, and the residual oil triturated with 20 ml of ether and 80 ml of petroleum ether. The solid was filtered and washed 3 times with water to give 2.64 g of crude product. Purification by chromatography on a 300 g silica gel column, packed in 80:20:1.5, CHCl$_3$:i-PrOH:H$_2$O by elution with 80:20:1.5 followed by 70:30:2.5, CHCl$_3$:i-PrOH:H$_2$O yielded 1.17 g of single spot product and 730 mg of sidecuts. A 20 hour acid hydrolysate gave the following amino acid analysis.

|  | Found μm/mg | Normalized to the average |
|---|---|---|
| Lys | 0.795 | 1.00 |
| Thr | 0.794 | 1.00 |
| Phe | 0.781 | 0.98 |
| Trp | 0.601 | 0.75 |
| Dsu | 0.820 | 1.03 |

R$_f$ 0.4, 80:20:2 (CMA)

EXAMPLE 7

Preparation of
ω-Methyl-α-t-butyl-N$_\alpha$-BOC-D-aminosuberate

Electrolytic oxidation of 7.9 g methyl glutarate and 8.2 g of N$_\alpha$-BOC-α-t-butyl-D-glutamate in 240 ml of MeOH and 80 ml of pyridine in the presence of 250 mg of Na was carried out as in Example 20, U.S. Ser. No. 695,348, filed June 14, 1976, for 1¾ hours. The brown solution was evaporated in vacuo to a viscous oil, which was partially redissolved in 25 ml CHCl$_3$. The insoluble material was centrifuged and the supernatant applied to a 700 g Silica Gel 60 column. The column was eluted with CHCl$_3$:EtOAc (97:3) and 125 ml fractions were collected. Fractions 36–48 were evaporated to give 2.97 g of product with R$_f$ values identical to the product described in Example 11, U.S. Ser. No. 695,348, filed June 14, 1976.

EXAMPLE 8

Preparation of ω-Methyl-α-t-butyl-D-aminosuberate

A solution of 1.25 g of BOC-ω-methyl-α-t-butyl-D-aminosuberate in 13 ml of EtOAc was treated with 26 ml of 4 N HCl in EtOAc at room temperature for 20 minutes. The solution was poured into cold saturated bicarbonate solution and the product extracted with three 110 ml portions of EtOAc. The combined EtOAC layers were dried over MgSO₄, filtered and evaporated in vacuo to give 760 mg of product.
$R_f$ 0.7, 90:10:1 (CMA)

EXAMPLE 9

Preparation of

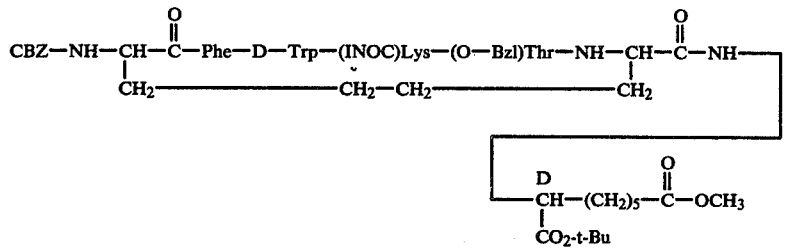

To a solution of 1.49 g of

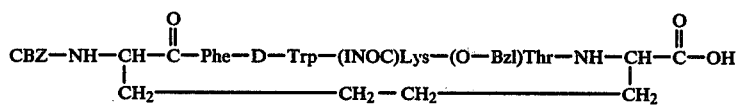

and 432 mg of ω-methyl-α-t-butyl-D-aminosuberate in 10 ml of DMF was added at −20° C. 0.35 ml DPPA and the reaction solution was kept at −20° C. for 20 hours and at +5° C. for 24 hours during which period 0.1 ml of DIPEA was added to keep the pH at 7.0–7.2. The mixture was filtered, and the filtrate evaporated to an oily residue which was triturated with ether to give 1.62 g of crude product. Purification by chromatography on a 170 g silica gel column, packed in 90:10:0.5, CHCl₃:i-PrOH:H₂O, which was eluted with the same solvent gave 1.45 g of product. A 20 hour acid hydrolysate gave the following amino acid analysis.

|  | Found μm/mg |
|---|---|
| Lys | 1.00 |
| Thr | 0.98 |
| Phe | 0.99 |
| Dsu | 1.01 |

|  | Found μm/mg |
|---|---|
| D-Asu | 1.00 |

$R_f$ 0.45, 90:10:0.5, (CHCl₃:i-PrOH:H₂O).

EXAMPLE 10

Preparation of

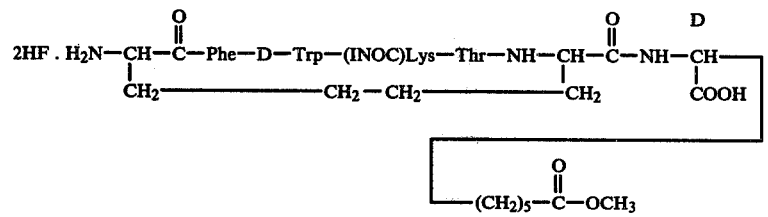

A mixture of 1.43 g of

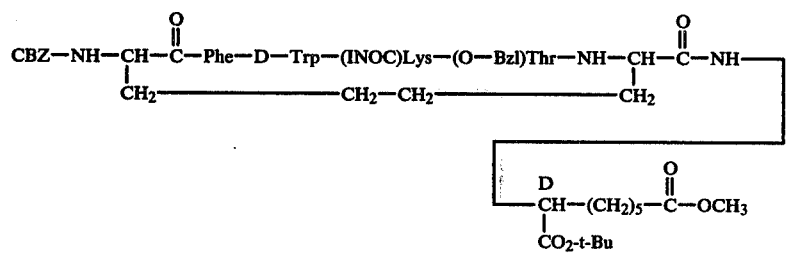

in 3 ml of anisole was treated with 30 ml of HF at 0° C. for 30 minutes. The HF was removed in vacuo at 0° C. and the oily residue triturated with 2 portions of a solution containing 10 ml of EtOAc and 50 ml of petroleum ether to give 1.18 g of product.
$R_f$ 0.6, 60:30:5 (CMW)

A 20 hour acid hydrolysis gave the following amino acid analysis.

|  | Found μm/mg | Normalized to the average |
|---|---|---|
| Lys | 0.694 | 1.03 |
| Thr | 0.630 | 0.94 |
| Phe | 0.671 | 1.00 |
| Trp | 0.651 | 0.97 |
| Dsu | 0.651 | 0.97 |

EXAMPLE 11

Preparation of

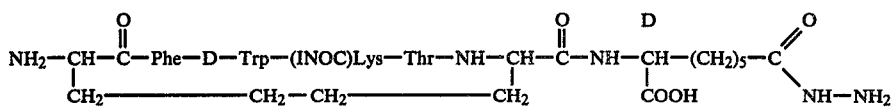

A solution of 1.1 g of

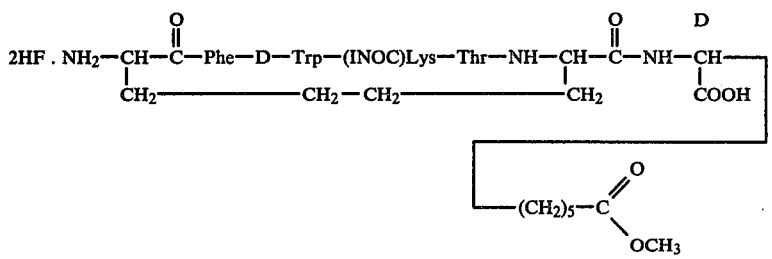

in 22 ml DMF was treated with 11 ml of hydrazine for 90 minutes at room temperature. The solution was evaporated to a small volume. Two portions of DMF were evaporated and the residue triturated with 3 portions of EtOAc. After drying, the solid was washed with water until the filtrate was negative to Tollen's reagent to give 700 mg of product.

The filtrate was freeze-dried to give an additional 510 mg of crude hydrazide. The water insoluble and water soluble products were purified separately by silica gel chromatography using a ratio of silica gel 60 to product ratio of 150:1. The products were charged in 60:30:5, (CMW) containing 2-5 drops $NH_2NH_2$, and eluted with the same solvent containing no $NH_2NH_2$. Product fractions from both columns were combined on the basis of tlc evaluation, evaporated to a small volume and the residue freeze-dried to give 750 mg of hydrazide.

A 20 hour acid hydrolysis gave the following amino acid anaylsis.

|     | Found μm/mg |
| --- | --- |
| Lys | 0.99 |
| $NH_3$ | 0.26 |
| Thr | 1.01 |

|     | Found μm/mg | Normalized to the average |
| --- | --- | --- |
| Asu | 0.639 | 0.95 |

|     |      |
| --- | ---- |
| Phe | 1.00 |
| Trp | 0.93 |
| Dsu | 1.00 |
| Asu | 1.03 |

HPLC in 55% $NH_4Ac$—$CH_3CN$ shows a 5-10% impurity.

EXAMPLE 12

Preparation of

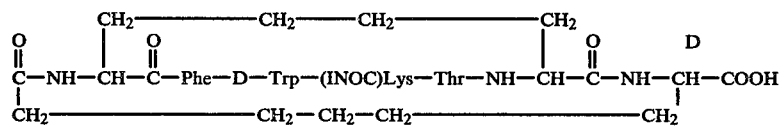

A solution of 750 mg of

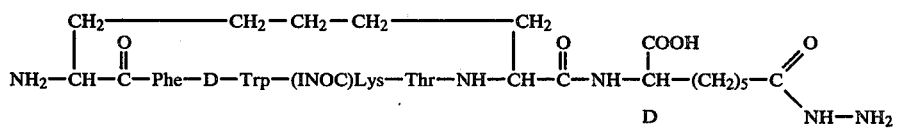

in 15 ml of DMF and 0.78 ml of 5.41 M HCl in THF was treated at $-25°$ C. with 0.115 ml of isoamyl nitrite for 1 hour and added to 750 ml of previously cooled and degassed DMF. The reaction was neutralized to 7.0 to 7.2 with 0.115 ml DIPEA and stored at $-20°$ C. for 18 hours and $+5°$ C. for 72 hours, during which period 0.3 ml DIPEA was added to keep the pH at 7.0 to 7.2.

The reaction solution was evaporated to a small volume and the residue triturated with EtOAC and petroleum ether and the solid washed with water to give 590 mg of insoluble product. The water washes were freeze-dried to give an additional 800 mg of crude product.

The water insoluble product was purified by Sephadex Gel filtration on a 5×100 cm column using Sephadex G-50 in 50% acetic acid. 17.5 ml fractions were collected and desired monomeric product was collected in fractions 99 to 107 to give 115 mg of product.

A 20 hour acid hydrolysate gave the following amino acid composition:

| | Found μm/mg | Normalized to the Average |
|---|---|---|
| Lys | 0.408 | 1.03 |
| Thr | 0.361 | 0.91 |
| Phe | 0.394 | 1.00 |
| Trp | 0.141 | 0.36 |
| Asu | 0.398 | 1.00 |
| Dsu | 0.387 | 0.98 |

EXAMPLE 13

Preparation of $$\underset{CH_2}{\overset{O}{\underset{\|}{C}}}-NH-\underset{|}{CH}-\overset{O}{\underset{\|}{C}}-Phe-D-Trp-Lys-Thr-NH-\underset{|}{CH}-\overset{O}{\underset{\|}{C}}-NH-\overset{D}{\underset{|}{CH}}-COOH$$
(with side chains CH₂—CH₂—CH₂—CH₂ and CH₂—CH₂—CH₂ and CH₂)

A suspension of 99 mg of

[analogous structure with (INOC)Lys]

in 7 ml of 50% acetic acid and 5 ml of ethanol and 82 mg of 10% palladium on charcoal was treated with hydrogen at 200 mm Hg pressure for 1 hour and 50 minutes. The reaction mixture was filtered and the filtrate evaporated to dryness. The residue was dissolved in 5 ml of 2 N AcOH and filtered through a 5×100 cm column of Sephadex G-25F in 2 N AcOH. The fractions containing the product were combined, evaporated and freeze-dried to give 36.3 mg of product.

$R_f$ 0.46 in 65:10:25, (BAW)
$R_f$ 0.27 in 10:5:1:3, (EPAW)
$R_f$ 0.51 in 60:40:10, (CMW)
$[\alpha]_D = -16.2°$ in (c 0.1, 50% AcOH)

A 20 hour acid hydrolysate gave the following amino acid analysis:

| | Found μm/mg | Normalized to the Average |
|---|---|---|
| Lys | 0.849 | 0.99 |
| Thr | 0.872 | 1.01 |
| Phe | 0.857 | 0.99 |
| Trp | 0.244 | 0.28 (0.97 by U.V.) |
| Asu | 0.881 | 1.02 |
| Dsu | 0.848 | 0.98 |

EXAMPLE 14

Preparation of $$[-NH-\underset{|}{CH}-\overset{O}{\underset{\|}{C}}-Phe-D-Trp-(INOC)Lys-Thr-NH-\underset{|}{CH}-\overset{O}{\underset{\|}{C}}-NH-\underset{|}{\overset{COOH}{\underset{D}{CH}}}-(CH_2)_5-\overset{O}{\underset{\|}{C}}-]_2$$

Fractions 83 to 96 from the Sephadex G-50 (50% acetic acid) column of Example 12 were combined, evaporated and lyophylized to give 381 mg of the title compound.

$R_f$ 0.5, 10:5:1:3 (EPAW).

A 20 hour acid hydrolysate gave the following amino acid composition:

| | Found μm/mg | Normalized to the Average |
|---|---|---|
| Lys | 0.641 | 1.03 |
| Thr | 0.564 | 0.90 |
| Phe | 0.625 | 1.00 |
| Trp | 0.416 | 0.67 |
| Asu | 0.63 | 1.01 |
| Dsu | 0.608 | 0.97 |

EXAMPLE 15

Preparation of $$[-NH-\underset{|}{CH}-\overset{O}{\underset{\|}{C}}-Phe-D-Trp-Lys-Thr-NH-\underset{|}{CH}-\overset{O}{\underset{\|}{C}}-NH-\underset{|}{\overset{COOH}{\underset{D}{CH}}}-(CH_2)_5-\overset{O}{\underset{\|}{C}}-]_2$$

A solution of 250 mg of

[analogous structure with (INOC)Lys]

in 6 ml of 50% acetic acid and 6 ml of ethanol and 150 mg of 10% palladium on charcoal was treated with hydrogen at 40 psig pressure for 1 hour. The reaction mixture was filtered and the filtrate evaporated to dryness. The residue was dissolved in 5 ml of 2 N AcOH and filtered through a 5×100 cm column of Sephadex G-25F in 2 N AcOH. The product was eluted with 2 N AcOH and 23.5 ml fractions were collected. The fractions 74 to 78 containing the product were combined, evaporated and freeze-dried to give 70.0 mg of product.
$R_f$ 0.3 in 10:5:1:3 (EPAW)
$R_f$ 0.54 in 60:40:10 (CMW)
A 20 hour acid hydrolysis gave the following amino acid analysis.

|  | Found μm/mg | Normalized to the Average |
|---|---|---|
| Lys | 0.758 | 1.01 |
| Thr | 0.759 | 1.01 |
| Phe | 0.745 | 0.98 |
| Dsu | 0.749 | 0.99 |
| Asu | 0.760 | 1.01 |
| Trp | 0.546 | 0.72 |

EXAMPLE 16

Preparation of the Mono-ε-(INOC) derivative of $$[-NH-CH(\overset{CH_2-------CH_2}{\underset{O}{|}})-\overset{O}{\overset{\|}{C}}-Phe-D-Trp-Lys-Thr-NH-CH(\overset{CH_2-------CH_2}{\underset{O}{|}})-\overset{O}{\overset{\|}{C}}-NH-\overset{COOH}{\underset{D}{C}}H-(CH_2)_5-\overset{O}{\overset{\|}{C}}-]_2$$

Fractions 66 to 70 from the Sephadex G-25 (2 N AcOH) column of Example 15 were combined, evaporated and freeze-dried to give 42 mg of the title product.
$R_f$ 0.7 in 60:40:10, (CMW)
$R_f$ 0.41 in 10:5:1:3, (EPAW)
A 20 hour acid hydrolysis gave the following amino acid analysis:

|  | Found μm/mg | Normalized to the Average |
|---|---|---|
| Lys | 0.760 | 1.01 |
| Thr | 0.738 | 0.98 |
| Phe | 0.755 | 1.00 |
| Dsu | 0.760 | 1.01 |
| Asu | 0.763 | 1.01 |
| Trp | 0.586 | 0.78 |

EXAMPLE 17

To prepare the compound having the structure:

$$\overset{O}{\overset{\|}{\underset{CH_2}{C}}}-NH-CH(\overset{CH_2-------CH_2-CH_2-CH_2-------CH_2}{\underset{\underset{CH_2-CH_2-CH_2-------CH_2}{|}}{|}})-\overset{O}{\overset{\|}{O}}-Phe-D-Trp-Lys-Thr-NH-CH-\overset{O}{\overset{\|}{C}}-NH-CH_2$$

methyl ω-aminoheptanoate was used instead of ω-methyl-α-t-butyl-D-aminosuberate in Example 8. In the cyclization step, the yield of monomeric product was increased and the reaction rate enhanced by cyclizing the azide (prepared from 820 mg of hydrazide) in 4.1 l of degassed DMF containing 4 g of HBT.H₂O. The product was isolated by evaporation in vacuo of the solvent and removal of HBT by trituration with aqueous bicarbonate solution. 500 mg of crude monomeric blocked product was obtained, 400 mg of which was deblocked by hydrogenation and purified by filtration through Sephadex G-50F (50% HOAc) and Sephadex 25F (2 N HOAc) to give 160 mg of final product.
$R_f$ 0.35 in 70:30:3, (CMA)
$R_f$ 0.59 in 10:5:1:3, (EPAW)
$[\alpha]_D$ −12.6 (c 0.1, 50% HOAc)
A 20 hour acid hydrolysis gave the following amino acid analysis:

|  | Found μm/mg | Normalized to the Average |
|---|---|---|
| Lys | 0.972 | 1.01 |
| Thr | 0.981 | 1.02 |
| Phe | 0.966 | 1.00 |
| Aha | 0.925 | 0.96 |
| Dsu | 0.067 | 1.00 |
| Trp | — | 1.00 (U.V.) |

The somatostatin analogs of the present invention and the non-toxic pharmaceutically acceptable salts thereof are useful in humans and animals for inhibiting growth hormone release as in the treatment of acromegaly. They are useful for inhibiting the release of glucagon and alone or in conjunction with insulin, for lowering blood glucose as in the treatment of diabetes. In the treatment of diabetes, the number and size of daily doses and the time of administration are determined by an individual study of each subject. The method of determining these factors is known to those skilled in the art.

The somatostatin analogs described herein may be administered to warm blooded animals, including humans, either intravenously, subcutaneously, intramuscularly or orally. The contemplated dose range for oral administration in tablet or capsule form to large mammals is about 0.001 mg to about 7 mg/kg of body weight per day. These somatostatin analogs are preferably administered by injection. A therapeutically effective amount of an analog is ordinarily supplied at a dosage level of from about 0.001 mg to about 2 mg/kg of body weight. Preferably the range is from about 0.00142 mg to about 0.428 mg/kg of body weight administered by intravenous infusion or by subcutaneous injection. The required dosage will vary with the particular condition being treated, the severity of the condition and the duration of treatment.

If the active ingredient is administered in tablet form, the tablet may contain: a binder such as gum tragacanth, corn starch, gelatin, an excipient such as dicalcium phosphate; a disintegrating agent such as corn starch and alginic acid; a lubricant such as magnesium stearate; and a sweetening and/or flavoring agent such as sucrose, lactose and wintergreen. Suitable liquid carriers for intravenous administration include sterile water, isotonic saline and phosphate buffer solutions or other pharmaceutically acceptable injectable carriers.

The following example is included to illustrate the preparation of a representative dose of

```
    CH2————————CH2—CH2————————CH2
 O  |           O                        O
 ‖  |           ‖                        ‖         D
 C—NH—CH—C—Phe—D—Trp—Lys—Thr—NH—CH—C—NH—CH—COOH
 |                                                |
 CH2——————————CH2 —CH2 —CH2—————————————CH2
``` suitable for subcutaneous injection.

EXAMPLE 18

1 ml. sterile saline;
1 mg

```
    CH2————————CH2—CH2————————CH2
 O  |           O                        O
 ‖  |           ‖                        ‖         D
 C—NH—CH—C—Phe—D—Trp—Lys—Thr—NH—CH—C—NH—CH—COOH
 |                                                |
 CH2——————————CH2 —CH2 —CH2—————————————CH2
```

What is claimed is:
1. The compound having the structure:

```
                                    CH2—————————CH2—CH2——————————CH2
    CH2—————————CH2—CH2                  |         O           W             |       O      Yα    O
         |         O           W             |       O             [—NH—CH—C—X—D(or L)—Trp—Lys—Thr—NH—CH—C—NH—CH—(CH2)5—C—]2
[—NH—CH—C—X—D(or L)—Trp—Lys—Thr—NH—CH—        CH2
                                    O      Yα    O
                                    —C—NH—CH—(CH2)5—C—]n
``` wherein
 n is 1 or 2;
 X is Phe or Tyr;
 Y is H or COOH and
 when Y is COOH, the carbon atom designated α in aminosuberyl is D- or L-;
 W on the ε-amino group of lysine is independently selected from H or INOC, and non-toxic pharmaceutically acceptable salts thereof.

2. The compound having the structure:

wherein
 X is Phe or Tyr;
 Y is H or COOH and
 when Y is COOH, the carbon atom designated α in aminosuberyl is D- or L-;
 W on the ε-amino group of lysine is H or INOC, and non-toxic pharmaceutically acceptable salts thereof.

3. The compound according to claim 1 having the structure:

wherein
 X is Phe or Tyr;
 Y is H or COOH and
 when Y is COOH, the carbon atom designated α in aminosuberyl is D- or L-;
 W on the ε-amino group of lysine is independently selected from H or INOC, and non-toxic pharmaceutically acceptable salts thereof.

4. The compound according to claim 3 having the structure:

```
    CH2————————CH2 — CH2————————CH2         COOH
         |          O          W             |       O       |D             O
[—NH—CH—C—Phe—D—Trp—Lys—Thr—NH—CH—C—NH—CH—(CH2)5—C—]2
``` wherein
 D refers to the D-isomer, and
 W on the ε-amino group of lysine is independently selected from H or INOC, and non-toxic pharmaceutically acceptable salts thereof.

5. The compound according to claim 3 having the structure:

```
    CH2————————CH2—CH2————————CH2
         |          O          W             |       O                      O
[—NH—CH—C—Phe—D—Trp—Lys—Thr—NH—CH—C—NH—CH2—(CH2)5—C—]2
```

```
 O    CH2————————CH2 — CH2——————————CH2
 ‖     |          O          W             |       O              α
 C—NH—CH—C—X—D(or L)—Trp—Lys—Thr—NH—CH—C—NH—CH—Y
 |                                                |
 CH2—————————CH2—CH2—CH2————————————CH2
``` wherein
 W on the ε-amino group of lysine is independently selected from H or INOC, and non-toxic pharmaceutically acceptable salts thereof.

6. The compound according to claim 2 having the structure:

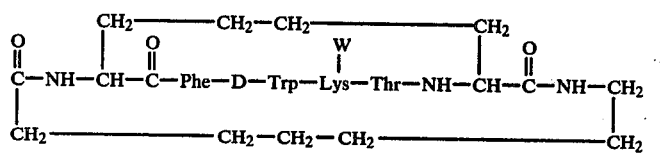

wherein
W on the ε-amino group of lysine is H or INOC, and non-toxic pharmaceutically acceptable salts thereof.

7. A compound according to claim 2 having the structure:

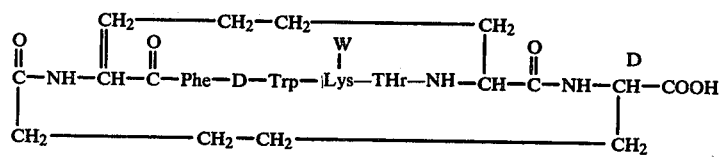

wherein

W on the ε-amino group of lysine is H or INOC, and non-toxic pharmaceutically acceptable salts thereof.

8. The compound having the structure:

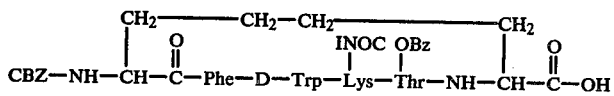

9. The compound having the structure:

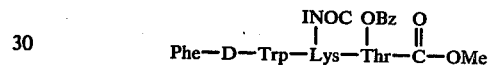

10. Compositions containing compounds of claim 1 and a pharmaceutically acceptable carrier.

* * * * *